(12) United States Patent
Jackson et al.

(10) Patent No.: US 10,159,913 B2
(45) Date of Patent: Dec. 25, 2018

(54) DEGASSING LIQUID ELUENT OF A PREPARATIVE SFC FLUID CHROMATOGRAPHY SYSTEM

(71) Applicant: Waters Technologies Corporation, Milford, MA (US)

(72) Inventors: Michael R. Jackson, Woonsocket, RI (US); Christopher Seith, Franklin, MA (US); Senthil Bala, Westborough, MA (US); Colin Fredette, Newton, MA (US); Maruth Sok, Providence, RI (US); Carlos Gomez, Ashland, MA (US); Joshua A. Shreve, Franklin, MA (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 52 days.

(21) Appl. No.: 15/333,876

(22) Filed: Oct. 25, 2016

(65) Prior Publication Data
US 2017/0136389 A1     May 18, 2017

Related U.S. Application Data

(60) Provisional application No. 62/246,326, filed on Oct. 26, 2015.

(51) Int. Cl.
| | |
|---|---|
| *B01D 19/00* | (2006.01) |
| *B01D 15/40* | (2006.01) |
| *G01N 30/14* | (2006.01) |
| *G01N 30/84* | (2006.01) |

(52) U.S. Cl.
CPC ......... *B01D 15/40* (2013.01); *B01D 19/0031* (2013.01); *G01N 30/84* (2013.01); *G01N 2030/8423* (2013.01)

(58) Field of Classification Search
CPC ................ B01D 15/40; B01D 19/0031; B01D 2257/504; G01N 30/84; G01N 2030/8423; G01N 30/80
See application file for complete search history.

(56) References Cited

U.S. PATENT DOCUMENTS

| | | | | |
|---|---|---|---|---|
| 4,958,529 A | * | 9/1990 | Vestal ..................... | G01N 30/84 250/288 |
| 5,242,471 A | * | 9/1993 | Markham ............. | G01N 30/462 73/23.37 |
| 5,340,384 A | * | 8/1994 | Sims .................. | B01D 19/0031 96/10 |

(Continued)

*Primary Examiner* — Jason M Greene
(74) *Attorney, Agent, or Firm* — Womble Bond Dickinson (US) LLP; Deborah M. Vernon; Heath T. Misley

(57) ABSTRACT

Methods, systems and apparatus are provided for degassing a supersaturated solution. An example degasser is described having a continuous body of gas-permeable tubing to remove an amount of a gas from the supersaturated solution below the gas's saturation point in the supersaturated solution. The degasser can be connected to at least one of a fraction collector or a detector. The example degasser is sized and/or positioned to cause a change in pressure (ΔP) across the degasser to drive removal of a dissolved gas from a supersaturated solution passing through the degasser. As a result of the reduction of gas, efficiencies in system flow and fraction collection are achieved.

18 Claims, 14 Drawing Sheets

(56) References Cited

U.S. PATENT DOCUMENTS

| | | | |
|---|---|---|---|
| 5,425,803 A * | 6/1995 | van Schravendijk | ........................ B01D 19/0031 95/46 |
| 5,980,742 A * | 11/1999 | Saitoh | ................ B01D 19/0031 210/186 |
| 6,248,157 B1 * | 6/2001 | Sims | .................. B01D 19/0031 95/46 |
| 6,379,796 B1 * | 4/2002 | Uenishi | ............. B01D 19/0031 428/375 |
| 2005/0092182 A1 * | 5/2005 | Thielen | .............. B01D 19/0031 96/6 |
| 2007/0012190 A1 * | 1/2007 | Gerner | ............... B01D 19/0031 96/6 |
| 2013/0061748 A1 * | 3/2013 | Sims | .................. B01D 19/0031 95/46 |
| 2015/0331001 A1 * | 11/2015 | Jones | ..................... B01D 15/40 436/71 |

\* cited by examiner

DEGASSING LIQUID ELUENT OF A PREPARATIVE SFC FLUID CHROMATOGRAPHY SYSTEM

RELATED APPLICATION

This application claims the benefit of and priority to U.S. Provisional Application No. 62/246,326 filed Oct. 26, 2015 and entitled "Degassing Liquid Eluent of a Preparative SFC Fluid Chromatography System," which is owned by the assignee of the instant application and the disclosure of which is hereby incorporated by reference in its entirety.

TECHNICAL FIELD

The present technology relates to a degasser for removing gas from a supersaturated solution. In particular, the present disclosure relates to methodologies, systems and apparatus for degassing a supersaturated solution within a degasser having gas-permeable tubing. The degasser can be used in carbon dioxide based chromatography preparative or analytical systems.

BACKGROUND OF THE TECHNOLOGY

In general, chromatography involves the flowing of a mobile phase over a stationary phase to effect separation. To speed-up and enhance the efficiency of the separation, pressurized mobile phases were introduced. For example, in carbon dioxide based chromatography systems, carbon dioxide or a carbon dioxide mixture is used as the extracting solvent in a supercritical or near supercritical fluid state. To keep the carbon dioxide in a supercritical or near supercritical fluid state the chromatography system is subjected to a predefined pressure. Most often, a back pressure regulator is employed downstream of the chromatography column to maintain the predefined pressure. Prior to entering the chromatography system a degasser or degasser unit is typically used to reduce the amount of dissolved gases in the mobile phase. After passing a mobile phase through a column to effect separation a resulting eluent may include dissolved gases due to the high system pressure. To remove a portion of the dissolved gases from the resulting eluent, the eluent typically passes through a gas-liquid separator. However, due to the system pressure required to use carbon dioxide or a carbon dioxide mixture (e.g. carbon dioxide mixed with a solvent such as methanol) in a supercritical or near supercritical fluid state, significant amounts of dissolved gas can remain in the eluent upon exiting the gas-liquid separator. High amounts of remaining dissolved gas can lead to outgassing (i.e., aerosolization) and interfere with subsequent flow and downstream processes, such as fraction collection and detection.

As such, there remains a need for robust and efficient degassing methods to minimize the outgassing of the mobile phase after separation and to enhance fraction collection yields and purity.

BRIEF SUMMARY OF THE TECHNOLOGY

The present technology relates to removing a portion of gas from a supersaturated solution. In particular, the embodiments of the present technology relate to degassing a supersaturated solution using a degasser in a chromatography based system, such as in carbon dioxide based chromatography, i.e., chromatography in which the mobile phase includes carbon dioxide.

The apparatus, systems and methods disclosed herein include a degasser formed, at least in part, of a gas-permeable material (e.g. polytetrafluoroethylene (PTFE), fluorinated ethylene propylene (FEP), polychlorotrifluoroethylene (PCTFE), polyvinylidene fluoride (PVDF)). The degasser of the present technology can be adapted (e.g., sized, shaped, positioned) to reduce or remove dissolved gas within a supersaturated solution below a gas saturation point for the particular supersaturated solution flowing through the degasser. In some embodiments, the degasser is not only formed from a gas-permeable material (e.g. a material permeable to the gas dissolved in the supersaturated solution), but also sized and positioned to provide a change in pressure ($\Delta P$) across the degasser to drive reduction of the dissolved gas from the supersaturated solution. As a result of reducing or removing the dissolved gas, less outgassing occurs resulting in a more consistent flow of the solution through the system and more efficient collection of the separated materials.

In one aspect, the present technology relates to a degasser, including a continuous body of gas-permeable tubing having an interior portion and an exterior portion and an inlet and an outlet for conducting the supersaturated solution through the continuous body of gas-permeable tubing; and at least one of a fraction collector or detector in fluid communication, either directly or indirectly, with the outlet of the continuous body of gas-permeable tubing, wherein the degasser removes an amount of gas below a gas's saturation point in the supersaturated solution.

Embodiments of the above aspect can include one or more of the following features. In one embodiment, a partial pressure of a component of the supersaturated solution decreases between the inlet and the outlet of the continuous body of gas-permeable tubing. In another embodiment, the continuous body of gas-permeable tubing is comprised of a polymeric material. The continuous body of gas-permeable tubing can be formed from a material which expands upon intake of the supersaturated solution. A change in pressure can occur between the interior portion and exterior portion of the continuous body of gas-permeable tubing. The gas-permeable tubing can be entangled. A vacuum source can be connected to the continuous body of gas-permeable tubing.

In another aspect, the present technology relates to a mixed fluid system, including a gas-liquid separator, a degasser and a mixer positioned upstream of both the gas-liquid separator and the degasser for introducing the supersaturated solution into the system. The degasser positioned downstream of the gas-liquid separator and comprising a continuous body of gas-permeable tubing having an interior portion and an exterior portion and an inlet and an outlet for conducting a supersaturated solution through the continuous body of gas-permeable tubing.

In a further aspect, the present technology relates to a method of degassing a supersaturated solution within a system, including flowing a supersaturated solution through a degasser, applying a change in pressure across at least a portion of the degasser to reduce a partial pressure of a component in the saturated solution and conducting the solution from the outlet of the degasser to a detector or a fraction collector. The degasser may include a continuous body of gas-permeable tubing having an interior portion and an exterior portion and an inlet and an outlet.

In yet a further aspect, the present technology relates to a method of degassing a supersaturated solution within a mixed fluid system, including a gas-liquid separator fluidly connected to a degasser, separating at least a portion of the supersaturated solution into a gas and a first liquid eluent within the gas-liquid separator, introducing the first liquid eluent from the gas-liquid separator into the inlet of the degasser, applying a differential pressure gradient across the degasser and separating an additional portion of the gas from the first liquid eluent, resulting in a second liquid eluent. The degasser including a continuous body of tubing, having an interior portion and an exterior portion, comprised of a gas-permeable material and having an inlet connected to the gas-liquid separator and an outlet.

Embodiments of the above aspect can include one or more of the following features. In one embodiment, the method further comprises directing the second liquid eluent to a collection vessel. In another embodiment, the second liquid eluent comprises a greater liquid to gas ratio by weight than the first liquid eluent.

In yet another further aspect, the present technology relates to a degasser for removing gas from a supersaturated solution, including a continuous body of gas permeable tubing including an inlet and an outlet for conducting the supersaturated solution through the continuous body and at least one of a fraction collector or detector in fluid communication with the outlet of the continuous body of tubing. The continuous body can be configured to have associated with it a residence time (g) of the supersaturated solution which can be adapted to remove an amount of gas from the supersaturated solution below a gas saturation point of the supersaturated solution.

The present technology provides a number of advantages over current methods, systems and apparatus. For instance, providing a degasser and downstream of a chromatography column and upstream of a fraction collector or detector can remove an amount of gas from the supersaturated solution (e.g., mobile phase) below a gas saturation point of the supersaturated solution while at the same time minimizing added volume to the system. That is, when the mobile phase enters a detector or fraction collector at ambient pressure the partial pressure of the dissolved phase will be below the saturation point. The present technology minimizes outgassing within the system and reduces splatter in collection vessels. As a result of reducing or removing the dissolved gas, less aerosolization occurs, resulting in more consistent system flow, better detection of peaks and more efficient collection of the separated materials.

BRIEF DESCRIPTION OF THE DRAWINGS

The foregoing and other features and advantages provided by the present technology will be more fully understood from the following description of exemplary embodiments when read together with the accompanying drawings.

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

DETAILED DESCRIPTION OF THE TECHNOLOGY

Figure 1A:
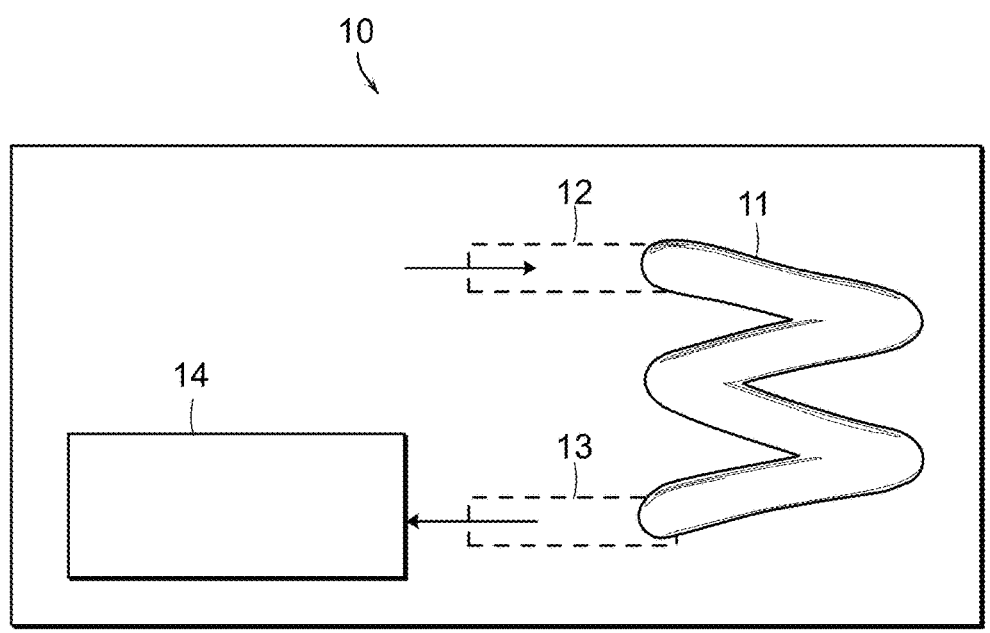
FIGS. 1A and 1B show example degassers, according to the principles of the present disclosure.

Following below are more detailed descriptions of various concepts related to, and embodiments of, inventive methods, apparatus, and systems for removing gas from a supersaturated solution using, inter alia, a continuous body of gas-permeable tubing. It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes.

As used herein, the term "includes" means includes but is not limited to, and the term "including" means including but not limited to. The term "based on" means based at least in part on.

The present technology relates to a degasser for removing a gas (e.g., carbon dioxide) from a supersaturated solution (e.g., mobile phase). Also provided herein, are methodologies and apparatus for degassing a supersaturated solution within a degasser and a system (e.g., mixed fluid system) that includes a degasser.

Outgassing, i.e., the spontaneous evolution of gas, of a supersaturated solution within a chromatography system can interfere with the amount of separated sample that reaches the collection vessel, as well as the resolution of two or more analytes of interest. In an example, a degasser according to the principles herein can be implemented for reducing of an amount of the dissolved gas in a supersaturated solution. Reducing the amount of dissolved gas in a supersaturated solution, before entering and/or after exiting the gas-liquid separator, can reduce outgassing. A reduction in outgassing can improve the separation integrity of the collected fractions. In one embodiment, the example degassers according to the principles herein can be adapted to reduce the outgassing of supersaturated solutions entering and/or exiting the gas-liquid separator, thereby enhancing the amount of separated sample that reaches the collection vessel and its purity.

In an example, degassers according to the principles herein can be adapted to reduce the outgassing of supersaturated solutions entering and/or exiting the gas-liquid separator. The rate of outgassing for a component can be computed based on an average outgassing rate, over a period, achievable using the component. The average outgassing rate can be computed based on a measure of the volume of the passageway of the component that admits the supersaturated solutions, the inner and outer surface area of the component, and measures of the rate of change of the pressure of the isolated component from a base pressure to a specified pressure. For example, the rate of change of pressure of the isolated component can be computed based on a rise time of the system from the base pressure to the specified pressure (providing a pressure differential). In an example, the outgassing rate can be computed based on the outgassing of a continuous body of gas-permeable tubing of the example degasser.

In an example, a system is provided that includes a degasser and a gas-liquid separator downstream of a chromatography column and upstream of a fraction collector or detector to remove an amount of gas from a supersaturated solution (e.g., mobile phase) below a gas saturation point of the supersaturated solution. The example degasser can be sized and positioned in the system such that a change in pressure ($\Delta P$) is derived across the degasser to drive reduction of the dissolved gas from the supersaturated solution. As a result of reducing or removing the dissolved gas, less aerosolization can occur, resulting in more consistent system flow and more efficient collection of the separated materials.

Degassing relates to the diffusion of a gas or gases through a permeable material. Diffusion processes are primarily of two main types: (a) steady state and (b) nonsteady state. Steady state diffusion can take place in a substantially even spatial distribution and at a constant rate, i.e., once the process starts, the number of atoms (or moles) crossing a given interface is constant with respect to time. Nonsteady state diffusion is a time dependent process in which the rate of diffusion is a function of time.

As used herein, the term "resolution" refers to the difference in retention of adjacent peaks divided by their average band width. Sufficient resolution between peaks is required for proper quantitation and efficient separation of different analytes. In some embodiments, an example system herein can be implemented to increase resolution by up to about 100%, about 90%, about 80%, about 70%, about 60%, about 50%, about 45%, about 40%, about 35%, about 30%, about 25%, about 20%, about 15%, or about 10%, as compared to similar systems that do not include the example degassers and other technology according to the principles herein.

As used herein, the term "phase" refers to the thermodynamic state of the mixture (e.g. liquid, gas, supercritical). A flow stream in a system in accordance with the present technology may include more than one phase. For example the flow stream can include a liquid phase and a gas phase (i.e., a "supersaturated solution"). In some embodiments, the mixed phase fluid, mixed phase fluid mixture, or mixed phase fluid stream can include about 1% liquid (such as but not limited to methanol), or about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, or more of a liquid. In some embodiments, the mixed phase fluid, mixed phase fluid mixture, or mixed phase fluid stream can include between about 0.0001% and 99.999% of liquid.

As used herein, the term "supersaturated solution" refers to a solution that includes a greater amount or proportion of a solute than would be present under normal conditions, including under atmospheric pressure and at ambient temperature. As a non-limiting example, carbonated water is a supersaturated solution of carbon dioxide gas in water. At atmospheric pressure, the carbon dioxide gas escapes slowly from the supersaturated liquid. However, at the elevated pressure of a sealed container (including a bottle), more carbon dioxide can be dissolved in the water than at atmospheric pressure.

As used herein, the term "mixed fluid system" refers to a system having a flow stream (including a flow stream of a supersaturated solution) that is capable of undergoing liquid/gas transitions within the system. As a non-limiting example, a mixed fluid system can include a carbon dioxide-based chromatographic system.

As used herein, the term "saturation point" refers to the point at which no higher amount of a substance (including a gas) can be absorbed into a vapor or dissolved into a solution, i.e., the vapor or solution includes the maximum concentration achievable of the particular substance under the given pressure and temperature conditions.

An example permeable surface or membrane allows materials (including liquids and gases) to pass through, either into or out of, the permeable surface. As used herein, "gas permeable" refers to a material, surface, or membrane that can allow passage of one or more of particles, ions, or water molecules there through. As used herein, "semi-permeable" refers to a surface or membrane that allows passage of some particles, ions, or water there through. In an example herein, a comparison between the passageway through a semi-permeable surface or membrane and the size of the material (such as but not limited to a particle, ion or fluid) desired to pass through the surface or membrane can be used to determine if the material can pass through the given semi-permeable surface or membrane. A non-permeable surface or membrane refers to one that does not allow particles, ions, or fluid to cross the material or membrane. In the technology of the present application, the semi-permeable surfaces or membranes are selected to allow fluids (e.g. gases) to pass through to reduce the partial pressures of a dissolved fluid from a supersaturated solution.

As used herein, the term "continuous body" refers to a physical structure that has an uninterrupted extension in space.

An example degasser according to the principles herein can include a continuous body of gas-permeable tubing having an interior portion and an exterior portion and an inlet and an outlet for conducting a supersaturated solution through the continuous body of tubing, and at least one of a fraction collector or detector in fluid communication, either directly or indirectly, with the outlet of the continuous body of tubing. The continuous body of gas-permeable tubing can be used to remove an amount of gas below a gas saturation point in the supersaturated solution.

An example continuous body of gas-permeable tubing of an example degasser can be formed from any of the gas permeable materials or membranes described herein. As non-limiting examples, the continuous body of gas-permeable tubing can be formed from a polytetrafluoroethylene (PTFE) material, a fluorinated ethylene propylene (FEP) material, a polychlorotrifluoroethylene (PCTFE) material, a polyvinylidene fluoride (PVDF) material, or an amorphous fluoroplastic polymer material.

The material selected and the size and shape of the continuous body of gas-permeable tubing is selected to achieve outgassing of a desired gas within a supersaturated solution below the gas saturation point. As an example, the continuous body of gas-permeable tubing of the degasser can be configured in any shape and/or size that is capable of reducing or removing an amount of a dissolved gas from a supersaturated solution, below a gas saturation point for the particular supersaturated solution, flowing through the degasser. In one example, the continuous body of gas-permeable tubing may be substantially coiled in shape (e.g., formed in a configuration of concentric rings). In another example, the continuous body of gas-permeable tubing may be substantially straight in shape, i.e., including at least a portion that extends uniformly in space. In yet other examples, the continuous body of gas-permeable tubing may be substantially non-uniform in shape, i.e., include portions that extend in a plurality of differing directions.

FIG. 1A shows an example degasser 10 according to the principles herein, which can be implemented for removing gas from a supersaturated solution. The example degasser 10 includes a continuous body of gas-permeable tubing 11 having an inlet 12 and an outlet 13 for conducting the supersaturated solution through the continuous body of gas-permeable tubing 11. The inlet 12 is illustrated as being adjacent to the outlet 13 in the example of FIG. 1A. However, other conformations are also within the scope of the instant disclosure. For example, an inlet 12 and an outlet 13 can be disposed at opposite sides of example degasser 10, or any other orientation relative to degasser 10. The example continuous body of gas-permeable tubing 11 has an interior portion and an exterior portion (described in greater detail in FIG. 4 herein below). Example degasser 10 also includes a component 14 in fluid communication, either directly or indirectly, with the outlet 13 of the continuous body of gas-permeable tubing 11. As an example, the component 14 can include a fraction collector or a detector, or can include both a fraction collector and a detector. The example degasser 10 can be implemented as described herein to remove an amount of a gas below the gas's saturation point in the supersaturated solution.

Figure 1B:
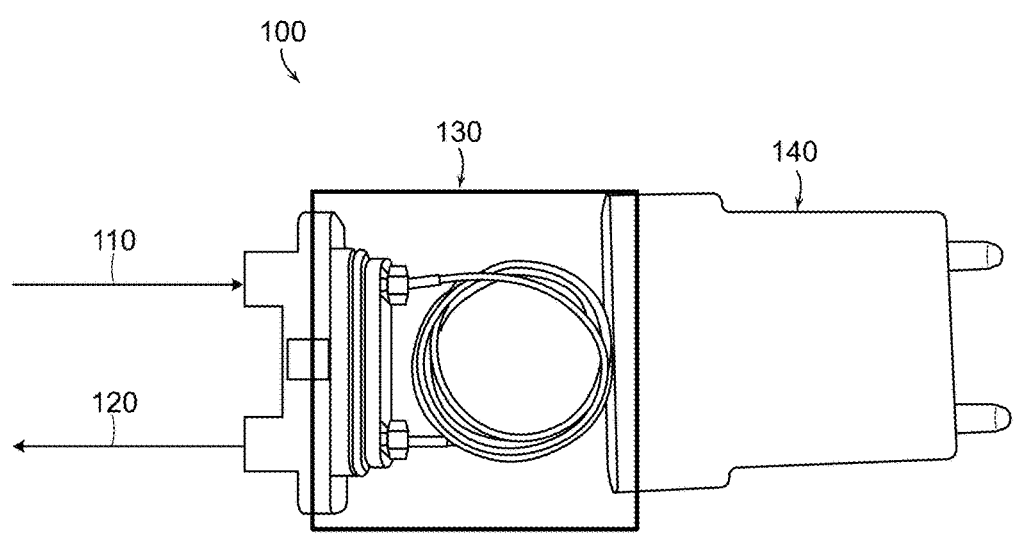

FIG. 1B shows another example degasser 100 according to the principle herein. Example degasser 100 includes a substantially coiled continuous body of gas-permeable tubing 130 having an inlet 110 and an outlet 120 for conducting the supersaturated solution through the continuous body of gas-permeable tubing 130. As shown in the example of FIG. 1B, the inlet 110 can be arranged adjacent to the outlet 120. In some non-limiting examples, the degasser 100 may be coupled to a vacuum source. FIG. 1B shows an example degasser 100 that includes a vacuum source 140. However, a vacuum source is not needed to create a change in pressure or to drive a reduction in partial pressure. And in some embodiments, a vacuum source is not desired.

In any example according to the principles herein, the gas-permeable tubing can be formed in an entangled conformation. As used herein, the term "entangled" refers to a body of tubing having at least a portion that includes a plurality of coils, folds, and/or loops. In an example, the plurality of coils, folds, and/or loops can be overlapping. Such an entangled body of tubing can be fabricated, at least in part, by weaving the tubing, in a plurality of directions, upon itself. An example entangled tubing herein can exhibit greatly increased surface area of the resulting body of tubing.

As a non-limiting example, the entangled body of tubing may be comprised of continuous small radius bends. The example entangled body of tubing may have an overall compact structure.

Figure 2:
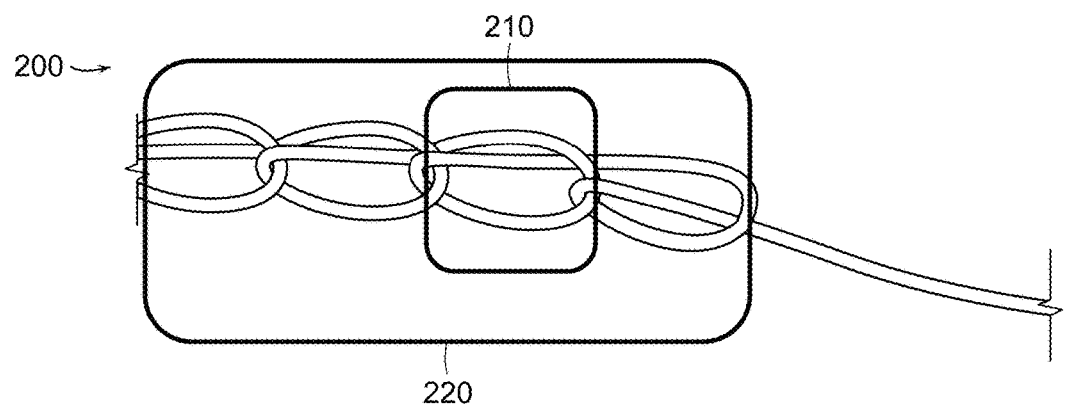
FIG. 2 shows an example section of a continuous body of entangled tubing, according to the principles of the present disclosure.

FIG. 2 shows an expanded view of a section of a non-limiting example continuous body of entangled tubing 200 and a single entangled "loop" 210. As shown in the example of FIG. 2, the entangled tubing 200 may be configured as a plurality of overlapping folds and/or loops. Exemplary embodiments of entangled tubing are also known in the art as "knit tubing" or "knitted tubing".

The continuous body of entangled tubing may be configured to produce a substantial turbulent flow, a substantial laminar flow, or some combination of both. In one embodiment, the continuous body of entangled tubing herein can be configured to reduce or minimize dispersion of the supersaturated solution flowing through the degasser.

Figure 3:
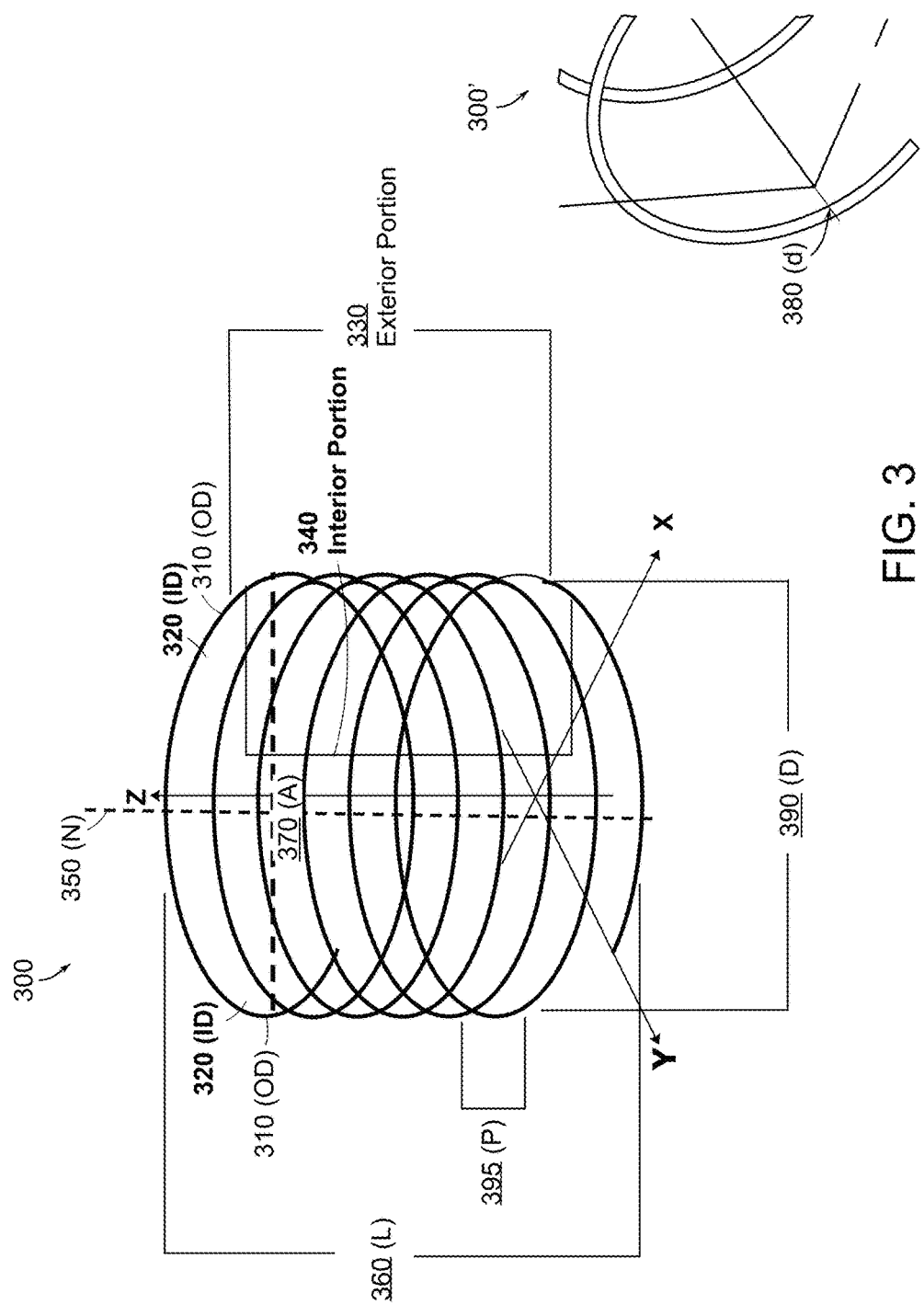
FIG. 3 shows a three dimensional view of an exterior portion and interior portion within a substantially coiled body of an example gas-permeable tubing, according to the principles of the present disclosure.

FIG. 3 shows an example of a substantially coiled tube forming a continuous body of gas-permeable tubing 300. The body of gas-permeable tubing 300 is shown having a central axis 350 or N parallel to the Z axis. The body of gas-permeable tubing can extend in a direction perpendicular with the Y axis (e.g. along the Y axis, X axis), or other direction. In the example of FIG. 3, the body of gas-permeable tubing is shown as having a helical conformation in the X-Y plane.

The "central axis" refers to a straight line about which the body of gas-permeable tubing may have rotational symmetry or that divides the body of gas-permeable tubing into symmetrical halves. As shown in FIG. 3, the central axis 350 or N may be perpendicular to the Y axis. In some embodiments, the central axis and body of gas-permeable tubing may be oriented perpendicular with respect to each other.

The continuous body of gas-permeable tubing according to the principles herein has an interior portion and a exterior portion. As shown in FIG. 3, the interior portion 340 and the exterior portion 330 can correspond to substantially opposite sides of the continuous body of tubing. As shown in FIG. 3, the radial distance of the outer dimension (310 or OD) to the central axis N is typically greater than the radial distance of the inner dimension (320 or ID) to the central axis N. In some examples, the exterior portion of the continuous body of tubing can include an outer perimeter wall. In other examples, the interior portion of the continuous body of tubing can include an inner bend radius. With reference to FIG. 3, the outer perimeter wall is located, for example, at OD or 310, whereas the interior perimeter wall is located at ID or 320.

As shown in FIG. 3, the body of gas-permeable tubing can be characterized by one or more of: the length or distance, L or 360, the inner cross sectional area, A or 370, inner diameter, d or 380, the outer diameter, D or 390, and the distance between consecutive coils (pitch), P or 395. The curvature ratio (d/D) can also be used to characterize the body of gas-permeable tubing.

Using the dimensions shown in FIG. 3, and the permeability of the material forming the continuous body of tubing, an average outgassing rate can be computed. Using the value of average outgassing rate, a measure of the degassing capability can be computed for an example degasser that includes the continuous body of tubing shown in FIG. 3.

In various non-limiting example implementations, the continuous body of tubing can be formed with a length (L) varying between about 0.5 inches and about 60 inches. Particularly, the length (L) can vary between about 5 inches and about 20 inches. In general, the length can be any length to accommodate system preferences.

In various non-limiting example implementations, the continuous body of tubing can be formed with an inner diameter (d) varying between about 0.005 inches and about 1 inch. Particularly, the inner diameter (d) can vary between about 0.03125 inches and about 0.625 inches. More particularly, the inner diameter (d) can vary between about 0.03125 inches and about 0.25 inches. In general, the inner diameter of the tubing is selected in accordance with the flow and resistance needs of a particular system. As a result, a wide variety of inner diameters (d) are available for use.

In various non-limiting example implementations, the tubing can be formed with a wall thickness (WT) between about 2.4 mm units and 6 mm. In general, the wall thickness (WT) is selected to prevent kinking of the tubing while at the same time allowing for flexibility to meet system preferences. As a result, a wide variety of wall thicknesses (WT) are available for use.

In various non-limiting example implementations, the continuous body of tubing can be formed with a pitch (p) and a curvature ratio (d/D) based upon system preference.

FIG. 3 shows an expanded view 300' of an example of a substantially coiled tube forming a continuous body of gas-permeable tubing 300. As shown in the example, the inner diameter, d or 380, is shown as measured in a direction parallel to the Z axis.

In some example implementations, the continuous body of gas-permeable tubing illustrated in FIGS. 3 and 3' can be formed with dimensional parameters (d, D, A and p) that remain substantially constant over the length, L. In other embodiments, one or more of these dimensions can be varied over the length, L. For example, the pitch p can be varied over the body of gas-permeable tubing length L, such that the pitch p exhibits a constant decrease or increase over L, or intermittent decrease or increase over L, or both. As another example, the variation in A can be a constant decrease or increase over L, intermittent decrease or increase over L, or both. As another example, the variation in d can be a constant decrease or increase over L, or intermittent decrease or increase over L, or both. As another example, the variation in D can be a constant decrease or increase over L, intermittent decrease or increase over L, or both. As another example, continuous body of gas-permeable tubing can be formed with both d and D increasing over the length of L, i.e., the coil can change in size over L. The percent increase for any one of these dimensions (d, D, A and p) over L can be up to 5%, 10%, 15%, 20%, 30%, 40%, 50%, 60%, 70%, 80%, 90%, or 100%. In one embodiment, the continuous body of gas-permeable tubing can be configured with a tightly coiled flow path such that over L, all four of the dimensional parameters (d, D, A and p) increase over the length L.

In various examples, the continuous body of gas-permeable tubing can be formed from any permeable material compatible with chromatography mobile phases, including carbon dioxide based chromatographic separation systems. The example continuous body of tubing can be formed from a non-polymeric material or a polymeric material. For example, the continuous body of tubing can be formed, at least in part, from a flexible chemical resistant polymer, such as but not limited to Teflon® tubing (a polytetrafluoroethylene commercially available from Dupont, Wilmington, Del.) and Teflon® AF tubing (a fluorinated ethylenic-cyclooxyaliphatic substituted ethylenic copolymer commercially available from Dupont, Wilmington, Del.).

In some embodiments, the gas permeable tubing can be infiltrated with a material to reduce friction. For example, the gas permeable tubing can be infiltrated, at least in part, with an amorphous carbon material, such as but not limited to diamond like carbon (DLC), or a hydrophobic silicone polymer, such as but not limited to Rain-X® (a glass surface treatment material that includes polyalkyl hydrogen siloxane, ethanol and isopropanol commercially available from SOPUS products). In general, the gas permeable tubing can be infiltrated with a vapor, liquid and/or gas to form a hydrophobic surface coating along the interior wall of the tubing.

In various examples, the material of the continuous body of tubing can be characterized by a value of Young's modulus (E), also referred to as an elasticity modulus or a tensile modulus. The value of modulus of a material provide a measure of a resistance of the material of the continuous body of tubing to elastic deformation (i.e., non permanent deformation) when subjected to an applied force. The modulus can be computed as a ratio of a stress (force per unit area) along an axis of the material to a strain (ratio of deformation over initial length) of the material along that axis or:

$$E \equiv \frac{\text{tensile stress}}{\text{extensional strain}} = \frac{\sigma}{\varepsilon} = \frac{F/A_0}{\Delta L/L_0} = \frac{FL_0}{A_0 \Delta L}$$

where:

$E$ is the Young's modulus (modulus of elasticity)

$F$ is the force exerted on an object under tension;

$A_0$ is the original cross-sectional area through which the force is applied;

$\Delta L$ is the amount by which the length of the object changes; and $L_0$ is the original length of the object.

The continuous body of tubing can be configured such that the flow of a supersaturated solution through the tubing can cause a circumferential force to be exerted from the interior diameter of the tubing (ID) (e.g., see tubing ID 410 in FIG. 4) to the outer diameter of the tubing (OD) (e.g., see tubing OD 420 in FIG. 4), and as a result cause the continuous body of tubing to expand. In one embodiment, the continuous body of gas-permeable tubing can be formed from a material that expands upon intake of the supersaturated solution. The material may expand uniformly or non-uniformly upon intake of the supersaturated solution. In another embodiment, the continuous body of gas-permeable tubing can be formed from a material that expands upon flowing the supersaturated solution through the continuous body of gas-permeable tubing. The expansion of the continuous body of gas-permeable tubing can affect the rate of diffusion of the supersaturated solution, thereby affecting the performance of the example degasser.

The continuous body of tubing can also be characterized by a value of the surface area to volume ratio. The surface area to volume ratio is the amount of surface area per unit volume of an object. The ratio imposes restrictions on the overall size, i.e., length, ID, OD and WT, of the continuous body of gas-permeable tubing. In general, a decrease in the surface area to volume ratio decreases the rate of diffusion through the continuous body of gas-permeable tubing and an increase in the ratio increases the rate of diffusion. As a result, the performance of the example degasser can be controlled based on the surface area to volume ratio of the continuous body of tubing.

Figure 4:
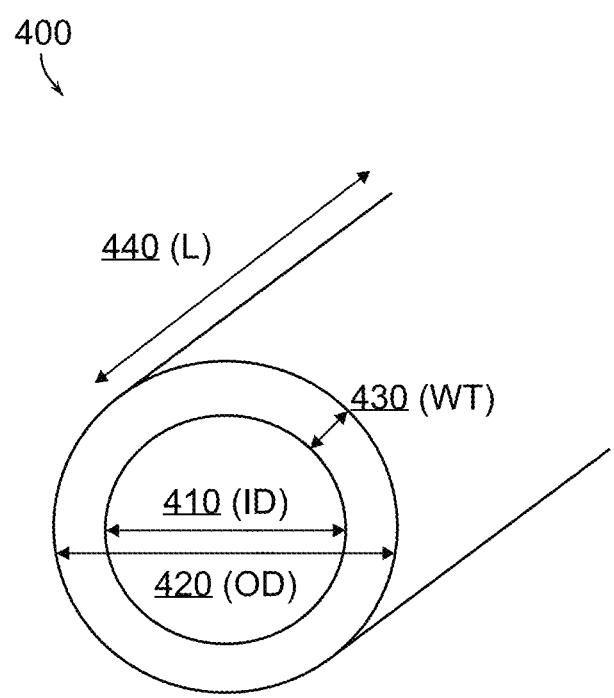
FIG. 4 shows a three dimensional view of an example section of gas-permeable tubing within the continuous body of gas-permeable tubing, according to the principles of the present disclosure.

As shown in FIG. 4, the tubing 400 including the continuous body of gas-permeable tubing can be characterized by one or more of: the length or distance, L or 440, inner diameter, ID or 410, the outer diameter, OD or 420, and the wall thickness WT or 430.

As shown in the examples of FIGS. 1A and 1B, the continuous body of gas-permeable tubing can include an inlet and an outlet for conducting the supersaturated solution through the continuous body of tubing. The inlet can be sized and shaped to efficiently and effectively receive the supersaturated solution. The outlet can be sized and shaped to efficiently and effectively discharge the supersaturated solution from the degasser. In some embodiments, including those illustrated in FIGS. 1A and 1B, the inlet and outlet are arranged adjacent to one another on the same side of the example degasser. In other embodiments, the inlet and outlet can be arranged at opposite sides of the example degasser.

In an example where the supersaturated solution is under reduced pressure, the supersaturated solution is capable of retaining less of the dissolved gases. As a result, the degasser can be used to remove a greater amount of the gas in the supersaturated solution. The reduction in pressure may be achieved as the result of evacuation using an applied vacuum. Example systems are described that include an example vacuum source coupled to the continuous body of gas-permeable tubing, to apply a vacuum to reduce the pressure at a region proximate to the continuous body of gas-permeable tubing. In some embodiments, the degasser may be connected to the example vacuum source. As shown in the example of FIG. 1B, the degasser 100 can also include a vacuum source 140. As gas from the supersaturated solution diffuses through a perimeter wall and exits the continuous body of gas-permeable tubing, the pressure within the body of tubing, for example proximate to the region at inner diameter (ID), may be lower than the pressure exerted on the outer portion of the body of tubing. That is, in an embodiment, the partial pressure of a component of the supersaturated solution can be decreased between the inlet and the outlet of the continuous body of gas-permeable tubing using the applied evacuation of a vacuum source. In some embodiments, the partial pressure of a component of the supersaturated solution can be decreased by about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, or more, between the inlet and the outlet of the continuous body of gas-permeable tubing.

The supersaturated solution can include a mobile phase flow, whole or partial, from an analytical or preparative chromatographic system. A component of the supersaturated solution can include, for example, carbon dioxide ($CO_2$). In one embodiment, the supersaturated solution is substantially the entire effluent flow from a preparative carbon dioxide based chromatographic system.

An example degasser including a continuous body of gas-permeable tubing can be used according to the principles herein to remove an amount of gas below a gas saturation point in the supersaturated solution. The continuous body of gas-permeable tubing can be used to remove an amount of gas of about 1%, about 2%, about 3%, about 4%, about 5%, about 6%, about 7%, about 8%, about 9%, about 10%, about 11%, about 12%, about 13%, about 14%, about 15%, 16%, about 17%, about 18%, about 19%, about 20%, about 25%, about 30%, about 35%, about 40%, about 45%, about 50%, about 55%, about 60%, about 65%, about 70%, about 75%, about 80%, about 85%, about 90%, about 95% or about 100%, below a gas saturation point in the supersaturated solution. In one embodiment, the continuous body of gas-permeable tubing can be used to remove an amount of gas below the saturation point of the gas at or near ambient temperatures and pressures.

Figure 5:
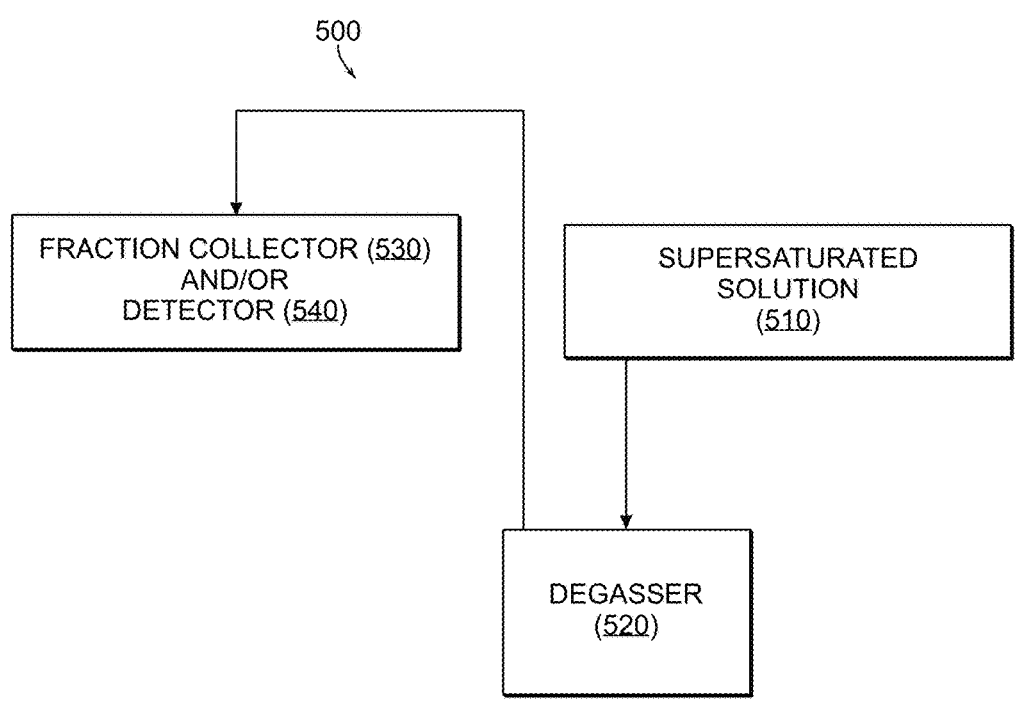
FIG. 5 is a block diagram of an example system, according to the principles of the present disclosure.

Example systems for degassing a supersaturated solution are described herein. FIG. 5 shows a block diagram of an example system 500 for removing an amount of a gas below the gas's saturation point in a supersaturated solution 510. The example system 500 includes a degasser 520 and at least one of a fraction collector 530 or detector 540. As a supersaturated solution (i.e., the mixed phase mobile phase) passes through degasser 520, a change in pressure ($\Delta P$) occurs due to the semipermeable material forming the degasser. As the mobile phase passes through degasser 520, the partial pressure of the mobile phase drops below the supersaturation point at or near ambient pressures as gas is driven out.

As a result of the degasser 520 reducing or removing the dissolved gas a more consistent system flow is achieved. This is because by removing the dissolved gas, the risk of extreme changes in flow rates or dispersion due to fluctuations generated by the dissolved or partially dissolved gas are minimized. As a further advantage of removing dissolved gas via the degasser 520, less outgassing occurs, which can result in better detection of peaks. An additional advantage of removing gas via the degasser 520 is a more efficient collection of the sample. For example, at a collection site, as system pressures drop a dissolved gas will quickly evaporate, creating an aerosol which can take away sample.

Figure 6:
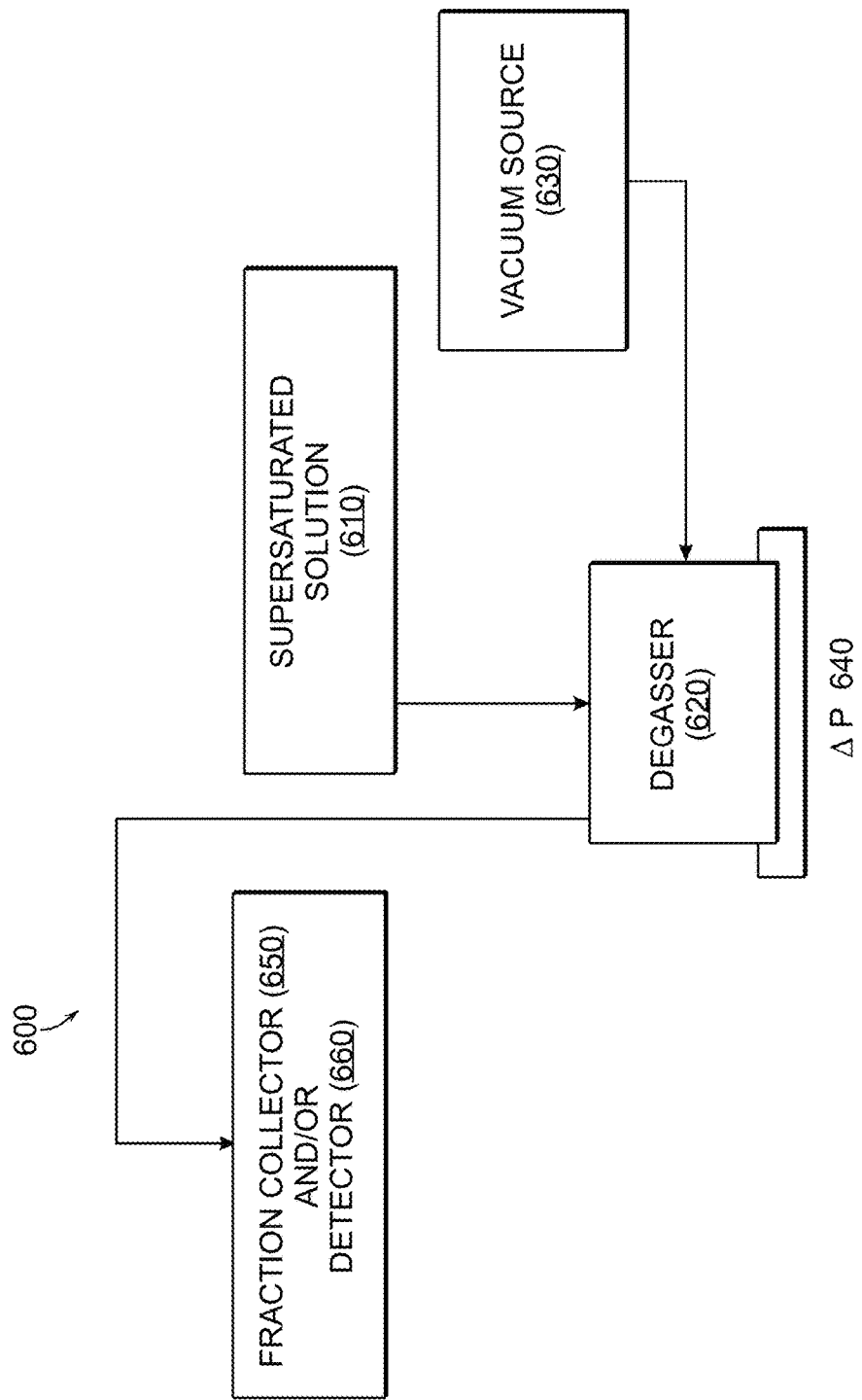
FIG. 6 is a block diagram of an example system that includes a vacuum source, according to the principles of the present disclosure.

FIG. 6 shows a block diagram of another example system 600 for removing an amount of a gas below the gas's saturation point in a supersaturated solution 610. The example system 600 includes a degasser 620, a fraction collector 650 or detector 660, and a vacuum source 630. In this example, the vacuum source 630 may be used to cause a change in pressure ($\Delta P$) 640 across at least a portion of the degasser 620.

Example systems for degassing a supersaturated solution are described herein that relate to a mixed fluid system. The example systems can include (i) a gas-liquid separator; (ii) a degasser and (iii) a mixer positioned upstream of both the gas-liquid separator and the degasser for introducing the supersaturated solution into the system. The example degasser can be positioned downstream of the gas-liquid separator. According to the principles herein, the example degasser can include a continuous body of gas-permeable tubing having an interior portion and an exterior portion and an inlet and an outlet for conducting a supersaturated solution through the continuous body of gas-permeable tubing. In one embodiment, the mixed fluid system can further include a chromatography column positioned upstream of both the gas-liquid separator and the degasser, but downstream of the mixer.

As a result of the example degasser reducing or removing the dissolved gas a more consistent system flow is achieved. This is because by removing the dissolved gas, the risk of extreme changes in flow rates or dispersion due to fluctuations generated by the dissolved or partially dissolved gas are minimized. As a further advantage of removing dissolved gas via the example degasser, less outgassing occurs, which can result in better detection of peaks. An additional advantage of removing gas via the example degasser is a more efficient collection of the sample. For example, at a collection site, as system pressures drop a dissolved gas will quickly evaporate creating an aerosol which can take away sample.

Figure 7:
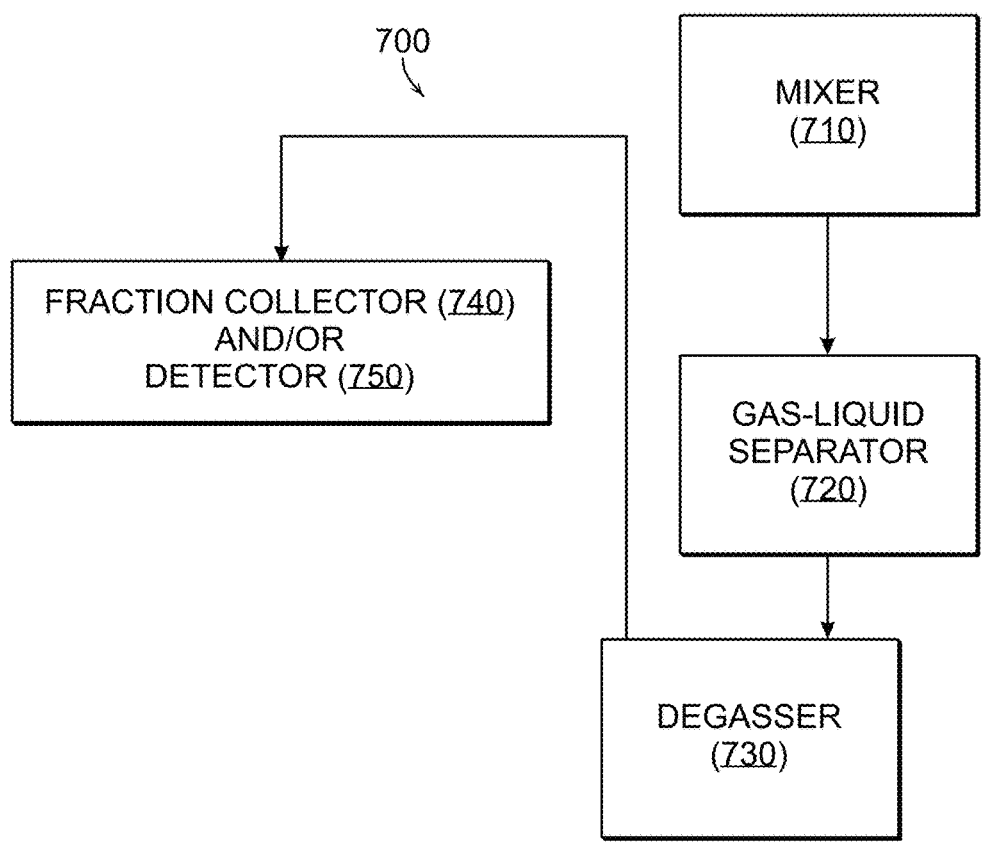
FIG. 7 is a block diagram of an example mixed fluid system, according to the principles of the present disclosure.

FIG. 7 shows a block diagram of an example first mixed fluid system 700 that includes a mixer 710, a gas-liquid separator 720, a degasser 730 and at least one of a fraction collector 740 or a detector 750.

Figure 8:
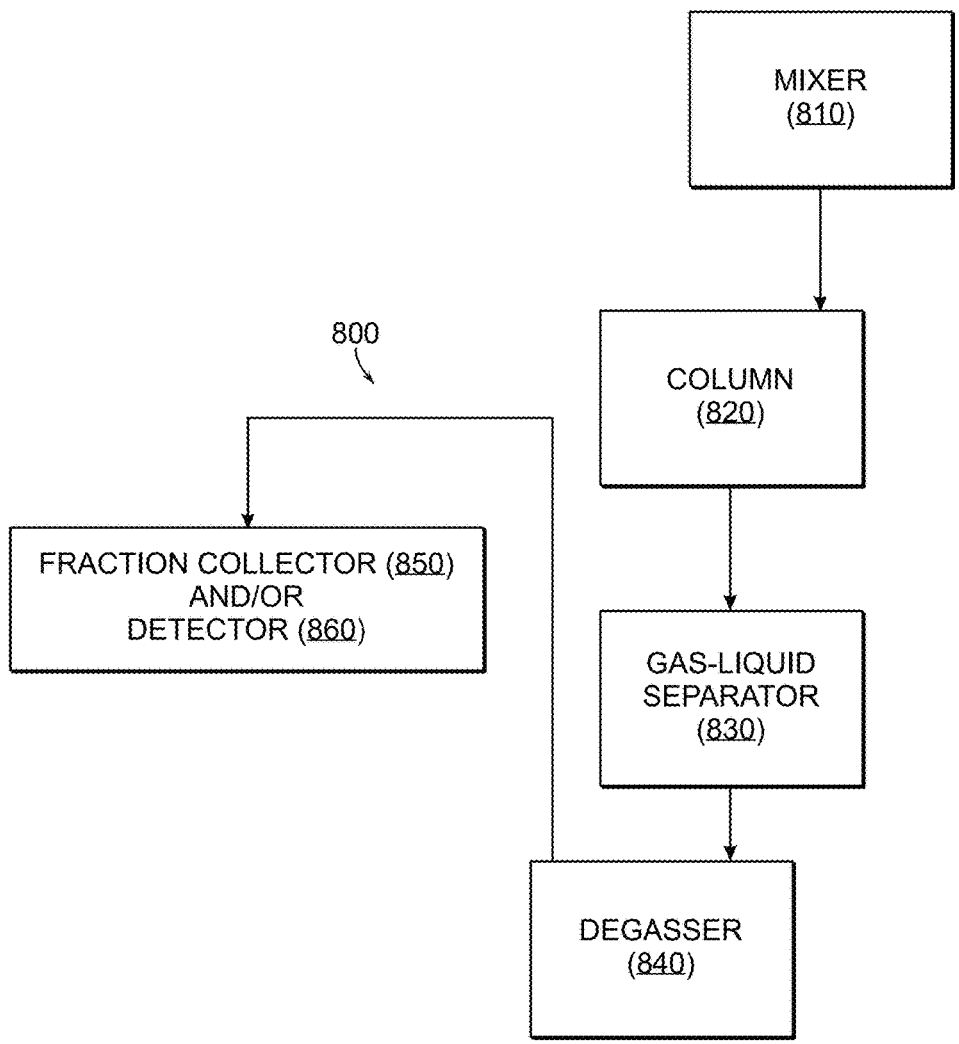
FIG. 8 is a block diagram of another example mixed fluid system, according to the principles of the present disclosure.

FIG. 8 shows a block diagram of another example mixed fluid system 800 that includes a mixer 810, a column 820, a gas-liquid separator 830, a degasser 840, and at least one of a fraction collector 850 or a detector 860.

Figure 9:
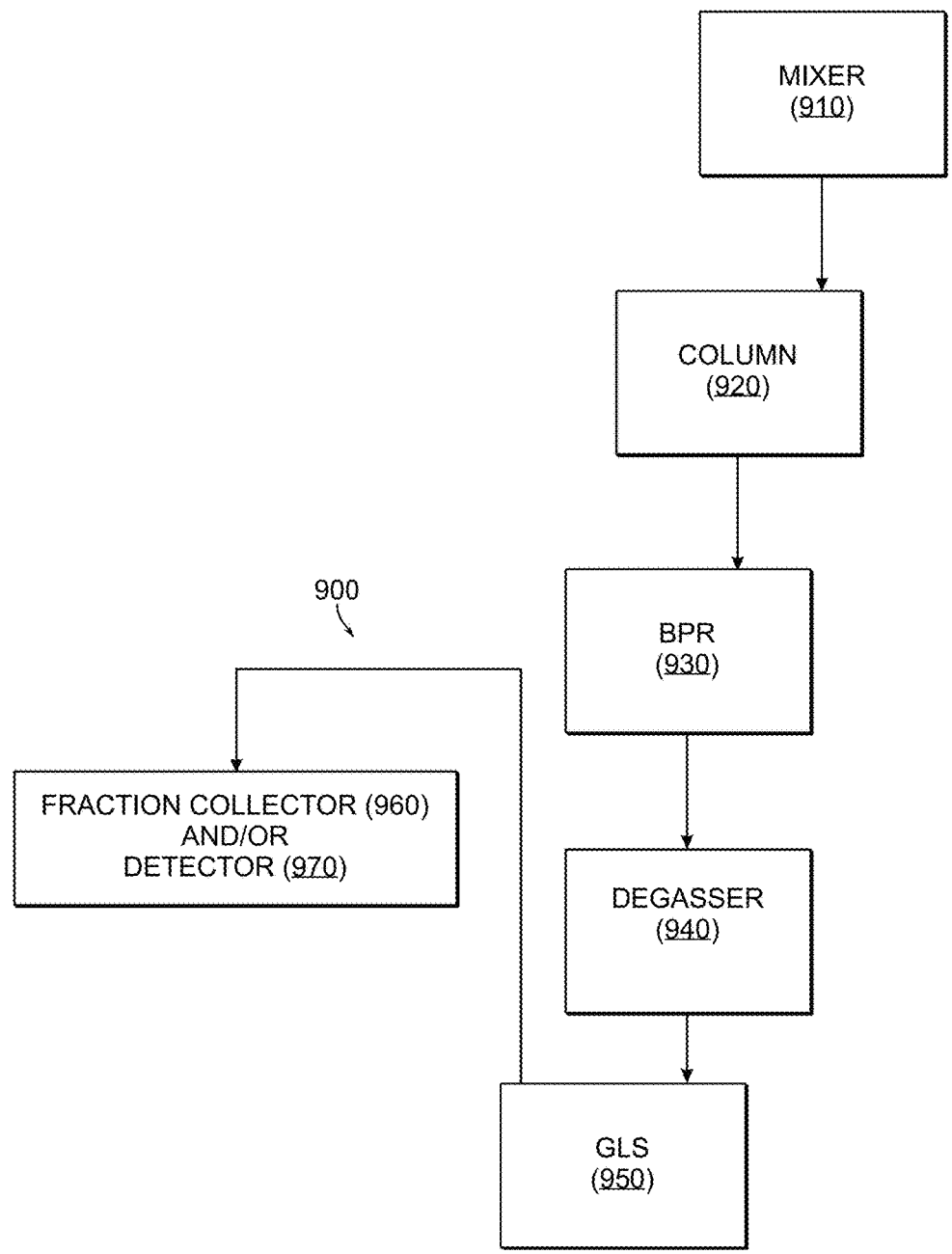
FIG. 9 is a block diagram of an example mixed fluid system that includes a back pressure regulator (BPR), according to the principles of the present disclosure.

FIG. 9 shows a block diagram of another example mixed fluid system 900 that includes a mixer 910, a column 920, a back pressure regulator (BPR) 930, a degasser 940, a gas-liquid separator (GLS) 950, and at least one of a fraction collector 960 or a detector 970.

Figure 10:
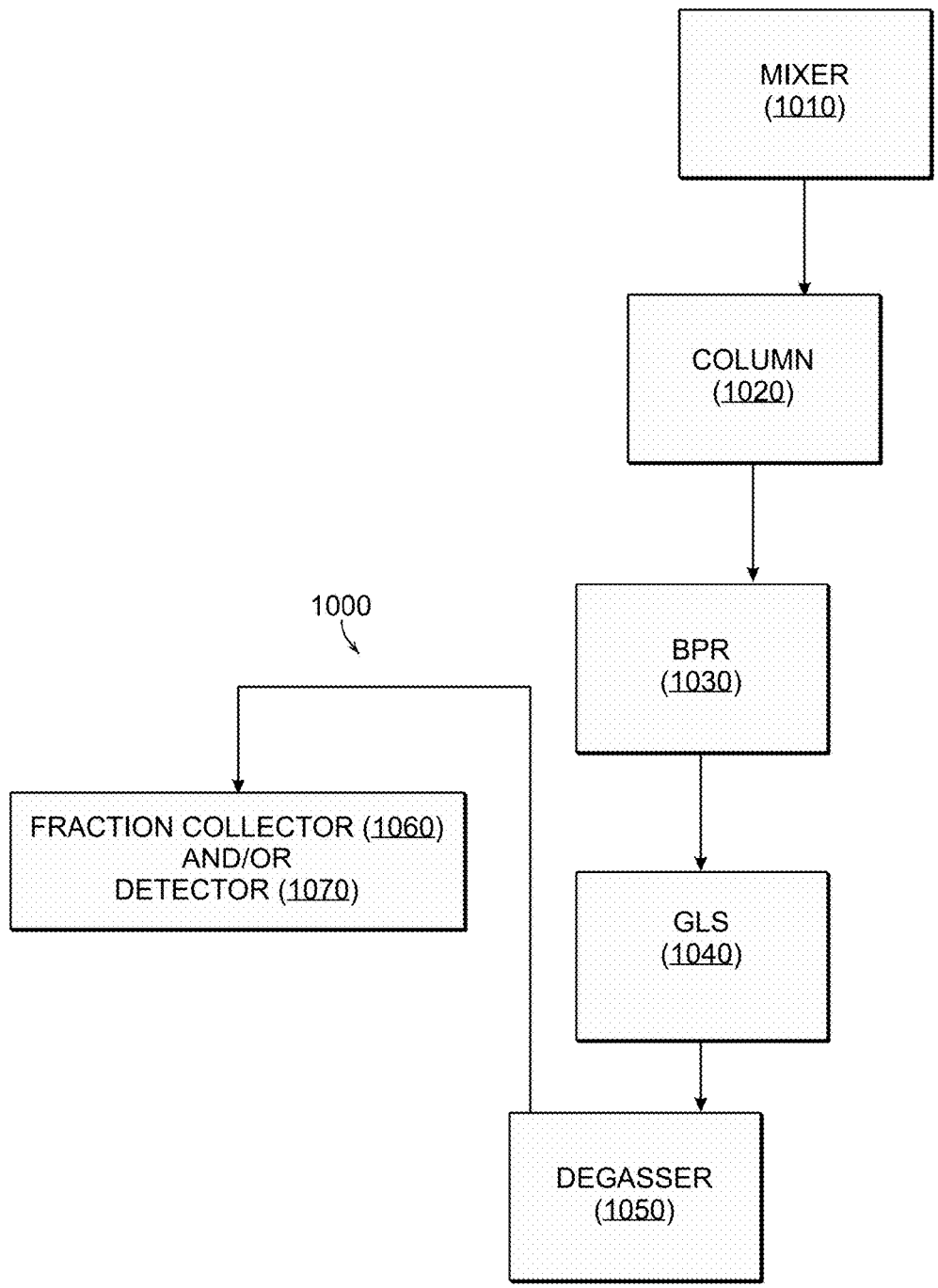
FIG. 10 is a block diagram of another example mixed fluid system, according to the principles of the present disclosure.

FIG. 10 shows a block diagram of another example mixed fluid system 1000 that includes a mixer 1010, a column 1020, a back pressure regulator 1030, a gas-liquid separator 1040, a degasser 1050, and at least one of a fraction collector 1060 or a detector 1070.

As shown in FIG. 10, an example system can include a degasser 1050 positioned downstream of the gas-liquid separator (GLS) 1040. As shown in FIG. 9, an example system can include a degasser 940 positioned upstream of the gas-liquid separator (GLS) 950.

The gas-liquid separator in the example systems can be any gas-liquid separator used in chromatography that can be used for separating a supersaturated solution into gas and liquid components. As non-limiting examples, the gas-liquid separator can be a cyclone (or centrifugal) separator, a gravity separator, filter vane separator, a mist eliminator pad or a liquid/gas coalescer.

The mixer used in the example systems can be any mixer used in chromatography that can be used for mixing at least two different fluid sources to create a mixed phase fluid mixture. As a non-limiting example, the mixer can be a static mixer, active mixer, turbulent flow mixer or packed bed mixer.

The fluid sources for any of the example systems herein can be any fluids used in chromatography that is capable of being mixed using a mixer to form a supersaturated solution. For example, a fluid source can be a carbon dioxide feed source or tank to supply one fluid as carbon dioxide, while another fluid source can be a methanol source to supply methanol. In another embodiment, a chromatography mobile phase can include water and acetonitrile. Under pressure, the acetonitrile can form tiny bubbles dissolved within the water. The degassers and methods of the present technology can be used to reduce the partial pressure of the dissolved acetonitrile to prevent splatter or other issues in a detector or other apparatus held at or near ambient temperature.

In another embodiment, example methods for degassing a supersaturated solution within a system are provided. An example method can include: (i) flowing a supersaturated solution through a degasser; (ii) applying a change in pressure across at least a portion of the degasser to reduce a partial pressure of a component in the saturated solution; and (iii) conducting the solution from the outlet of the degasser to a detector or a fraction collector. The example degasser can include a continuous body of gas permeable tubing having an interior portion and an exterior portion and an inlet and an outlet. In one embodiment, the degasser can be positioned downstream of the gas-liquid separator. In another embodiment, the degasser can be positioned upstream of the gas-liquid separator.

Figure 11:
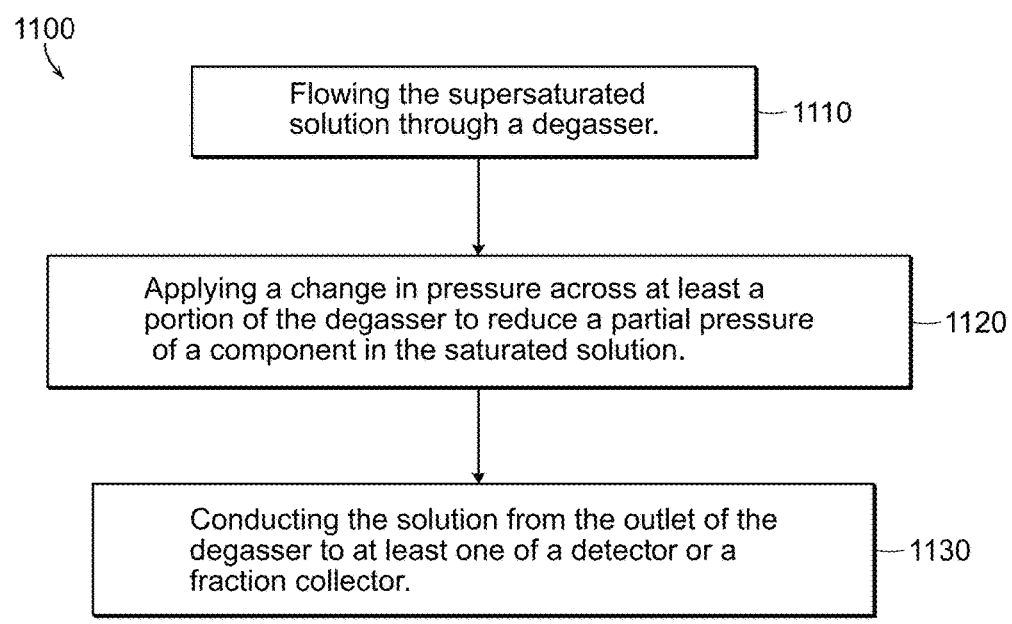
FIG. 11 is a flow chart of an example method for degassing a supersaturated solution using a degasser, according to the principles of the present disclosure.

FIG. 11 is a flow chart of a first example method 1100 for degassing a supersaturated solution using an example system. The example method includes flowing a supersaturated solution through a degasser (block 1110); applying a change in pressure across at least a portion of the degasser to reduce a partial pressure of a component in the saturated solution (block 1120); and conducting the solution from the outlet of the degasser to at least one of a fraction collector or a detector (block 1130).

Applying a change in pressure (e.g., block 1120) can be accomplished in various ways. For example, by flowing a supersaturated solution through a degasser formed of gas-permeable tubing gas is released resulting in a change of pressure. Additionally, a pressure gradient applied across the degasser 1100 can create the change in pressure to force the partial pressure of the saturated solution below the saturation point. Further, a vacuum or pressure source can be supplied across a portion of the degasser 1100 to change the pressure.

In an example method, the saturated solution can be introduced to the example system using any standard technique for managing fluid flow in chromatography. The saturated solution can be passed through the degasser by directing substantially all, a substantial portion of, or a fraction of the flow to the flow path.

In a further embodiment, example methods for degassing a supersaturated solution within a mixed fluid system are provided. An example method can include: (i) providing a gas-liquid separator fluidly connected to a degasser; (ii) separating at least a portion of the supersaturated solution into a gas and a first liquid eluent within the gas-liquid separator; (iii) introducing the first liquid eluent from the gas-liquid separator into the inlet of the degasser; (iv) applying a differential pressure gradient across the degasser; and (v) separating an additional portion of the gas from the first liquid eluent, resulting in a second liquid eluent. The example degasser can include a continuous body of gas-permeable tubing, having an interior portion and an exterior portion, formed from a gas-permeable material, and having an outlet and an inlet. The inlet of the example continuous body of gas-permeable tubing of the example degasser can be connected to the gas-liquid separator and an outlet.

Figure 12:
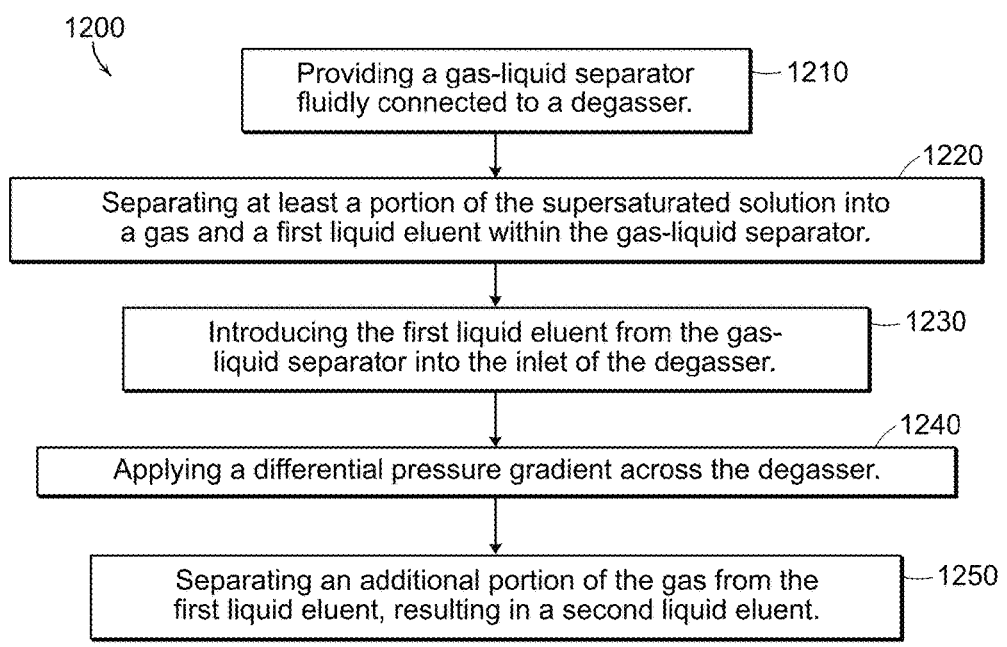
FIG. 12 is a flow chart of another example method for degassing a supersaturated solution using a degasser, according to the principles of the present disclosure.

FIG. 12 shows a flow chart of an example method 1200 for degassing a supersaturated solution within an example mixed fluid system. The example method 1200 can include: providing a gas-liquid separator fluidly connected to a degasser (block 1210); separating at least a portion of the supersaturated solution into a gas and a first liquid eluent within the gas-liquid separator (block 1220); introducing the first liquid eluent from the gas-liquid separator into the inlet of the degasser (block 1230); applying a differential pressure gradient across the degasser (block 1240); and separating an additional portion of the gas from the first liquid eluent, resulting in a second liquid eluent (block 1250).

In one embodiment, the method can further include directing the second liquid eluent to a collection vessel. In one embodiment, the second liquid eluent can include a greater liquid to gas ratio by weight than the first liquid eluent.

In yet another embodiment, an example degasser for removing gas from a supersaturated solution is provided that includes: (i) a continuous body of gas-permeable tubing including an inlet and an outlet for conducting the supersaturated solution through the continuous body and (ii) at least one of a fraction collector or detector in fluid communication with the outlet of the continuous body of tubing. The example continuous body of gas-permeable tubing can be configured to facilitate a residence time (g) that is adapted to remove an amount of gas from the supersaturated solution below a gas saturation point of the supersaturated solution.

In any example herein, the residence time (g) can be computed as the average amount of time that it takes for movement of the supersaturated solution through the continuous body of gas-permeable tubing. For example, the residence time (g) can be computed based on a flow velocity and the dimensions of the continuous body of gas-permeable tubing. In some examples, a residence time distribution function can be computed that describes the concentration of an analyte in the mobile phase as function of time and position in the body of tubing.

In some embodiments, the residence time (g) can vary between about 0.5 seconds and about 120 seconds. Particularly, the residence time (g) can vary between about 0.5 seconds and about 60 seconds. More particularly, the residence time (g) can vary between about 0.5 seconds and about 45 seconds.

Figure 13:
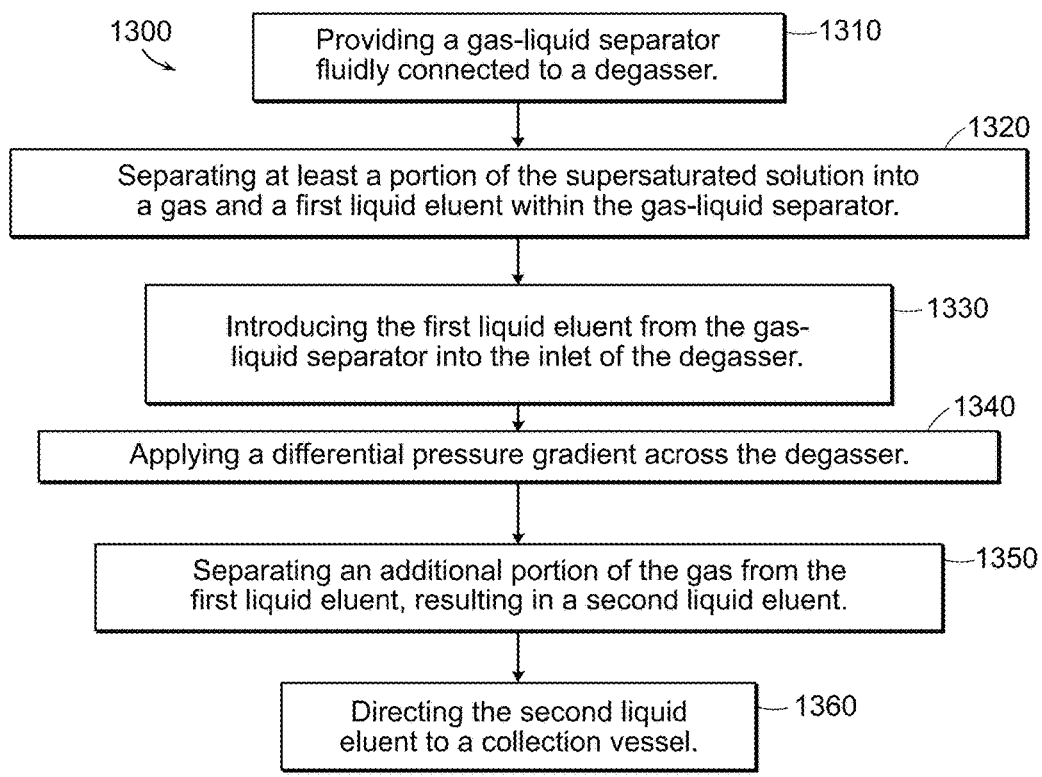
FIG. 13 is a flow chart of another example method for degassing a supersaturated solution using a degasser, according to the principles of the present disclosure.

FIG. 13 shows a flow chart of another example method 1300 for degassing a supersaturated solution within an exemplary mixed fluid system. Example method 1300 can include: providing a gas-liquid separator fluidly connected to a degasser (block 1310); separating at least a portion of the supersaturated solution into a gas and a first liquid eluent within the gas-liquid separator (block 1320); introducing the first liquid eluent from the gas-liquid separator into the inlet of the degasser (block 1330); applying a differential pressure gradient across the degasser (block 1340); separating an additional portion of the gas from the first liquid eluent, resulting in a second liquid eluent (block 1350); and directing the second liquid eluent to a collection vessel (block 1360).

The disclosures of all cited references including publications, patents, and patent applications are expressly incorporated herein by reference in their entirety for disclosure that is consistent with the description herein.

When an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the present technology be limited to the specific values recited when defining a range. The example systems, methods, and apparatus described herein can be further defined in the following non-limiting example implementations. It should be understood that these example implementations, while indicating preferred embodiments of the technology, are given by way of illustration only.

Non-Limiting Example Implementations

EXAMPLE 1

Degasser Including Amorphous Fluoroplastic Polymer Tubing

A supersaturated solution in a mixed fluid system is degassed using a degasser including a continuous body of gas-permeable tubing formed at least in part from an amorphous fluoroplastic polymer, such as but not limited to the TEFLON® AF amorphous fluoroplastic (a fluorinated ethylenic-cyclooxyaliphatic substituted ethylenic copolymer available from DuPont, Wilmington, Del.). The mixed fluid system includes, such as the system shown in FIG. 7, a mixer 710, a gas-liquid separator 720, a degasser 730 and at least one of a fraction collector 740 or a detector 750. The supersaturated solution includes a mixture of 95% carbon dioxide and 5% methanol by volume, at room temperature and 1 bar. The supersaturated solution is degassed in the degasser 730 after separation in the gas liquid separator. The degasser 730 in this example is formed of a continuous body of gas-permeable amorphous fluoroplastic polymer tubing, such as that shown in FIG. 1B.

EXAMPLE 2

Degasser Including Entangled (or Knitted) Amorphous Fluoroplastic Polymer Tubing A supersaturated solution in a mixed fluid system is degassed using a degasser including a continuous body of entangled gas-permeable tubing formed at least in part from an amorphous fluoroplastic polymer, such as but not limited to the TEFLON® AF amorphous fluoroplastic (a fluorinated ethylenic-cyclooxyaliphatic substituted ethylenic copolymer commercially available from Dupont, Wilmington, Del.). The mixed fluid system includes, such as the system shown in FIG. 7, a mixer 710, a gas-liquid separator 720, a degasser 730 and at least one of a fraction collector 740 or a detector 750. The supersaturated solution includes a mixture of 95% carbon dioxide and 5% methanol by volume, at room temperature and 1 bar. The supersaturated solution is degassed in the degasser 730 after separation in the gas liquid separator. The degasser 730 in this example is formed of a continuous body of entangled gas-permeable amorphous fluoroplastic polymer tubing, such as that shown in FIG. 2.

While this technology has been particularly shown and described with reference to example embodiments thereof, it will be understood by those skilled in the art that various changes in form and details may be made therein without departing from the scope of the technology encompassed by the appended claims.

What is claimed:

1. A degasser for removing gas from a supersaturated solution, comprising:
   (i) a continuous body of gas-permeable tubing having an interior portion and an exterior portion and an inlet and an outlet for conducting the supersaturated solution through the continuous body of gas-permeable tubing; and
   (ii) a fraction collector in direct fluid communication with the outlet of the continuous body of gas-permeable tubing, wherein the degasser removes a portion of the gas below the saturation point of the gas in the supersaturated solution.

2. The degasser of claim 1, wherein a partial pressure of a component of the supersaturated solution decreases between the inlet and the outlet of the continuous body of gas-permeable tubing.

3. The degasser of claim 1, wherein the continuous body of gas-permeable tubing is comprised of a polymeric material.

4. The degasser of claim 3, wherein the continuous body of gas-permeable tubing is formed from a material which expands upon intake of the supersaturated solution.

5. The degasser of claim 1, wherein a change in pressure occurs between the interior portion and exterior portion of the continuous body of gas-permeable tubing.

6. The degasser of claim 1, wherein the gas-permeable tubing is entangled.

7. The degasser of claim 1, further comprising a vacuum source connected to the continuous body of gas-permeable tubing.

8. A method of degassing a solution within a system, the method comprising:
  (i) flowing a solution through a degasser, the degasser comprising a continuous body of tubing, having an interior portion and an exterior portion, comprised of a gas permeable material, the degasser having an inlet and an outlet;
  (ii) applying a change in pressure across at least a portion of the degasser to reduce a partial pressure of a component in the solution; and
  (iii) conducting the solution from the outlet of the degasser directly to an inlet of a fraction collector.

9. The method of claim 8, wherein the partial pressure of a component in the solution will be below the supersaturation point of the solution at operative temperature and pressure conditions at or about an inlet of a detector or inlet of the fraction collector.

10. The method of claim 8, wherein a detector or the fraction collector are at ambient pressure and temperature.

11. The method of claim 8, wherein a change in pressure occurs between the outlet of the degasser and an inlet of a detector or the inlet of the fraction collector.

12. The method of claim 11, wherein the pressure decreases between the outlet of the degasser and an inlet of a detector or the inlet of the fraction collector.

13. The method of claim 8, wherein a change in temperature occurs between the outlet of the degasser and an inlet of a detector or the inlet of the fraction collector.

14. The method of claim 13, wherein the temperature increases between the outlet of the degasser and an inlet of the of a detector or the inlet of the fraction collector.

15. A method of degassing a supersaturated solution within a mixed fluid system, comprising:
  (i) providing a gas-liquid separator fluidly connected to a degasser, the degasser comprising a continuous body of tubing, having an interior portion and an exterior portion, comprised of a gas permeable material, the degasser having an inlet connected to the gas-liquid separator and an outlet;
  (ii) separating at least a portion of the supersaturated solution into a gas and a first liquid eluent within the gas-liquid separator;
  (iii) introducing the first liquid eluent from the gas-liquid separator into the inlet of the degasser;
  (iv) applying a differential pressure gradient across the degasser;
  (v) separating an additional portion of the gas from the first liquid eluent, resulting in a second liquid eluent; and
  (vi) conducting the second liquid eluent from an outlet of the degasser directly to an inlet of a fraction collector.

16. The method of claim 15, wherein the second liquid eluent comprises a greater liquid to gas ratio by weight than the first liquid eluent.

17. The degasser of claim 1 wherein the continuous body has a residence time (g) adapted to remove the portion of the gas below the saturation point of the gas in the supersaturated solution.

18. The method of claim 8, wherein the solution introduced to the degasser is a supersaturated solution.

* * * * *